United States Patent [19]

Kiyoura

[11] 4,247,716

[45] Jan. 27, 1981

[54] PROCESS FOR PRODUCING PYRUVIC ACID

[75] Inventor: Tadamitsu Kiyoura, Kamakura, Japan

[73] Assignee: Mitsui Toatsu Chemicals, Inc., Tokyo, Japan

[21] Appl. No.: 932,938

[22] Filed: Aug. 11, 1978

[30] Foreign Application Priority Data

Sep. 2, 1977 [JP] Japan ............................ 52-104765
Nov. 25, 1977 [JP] Japan ............................ 52-140599
Apr. 4, 1978 [JP] Japan ............................ 53-38758
Apr. 4, 1978 [JP] Japan ............................ 53-38757

[51] Int. Cl.$^3$ .................. C07C 51/235; C07C 59/19
[52] U.S. Cl. ................................ 562/513; 562/527; 562/577
[58] Field of Search ............ 562/527, 538, 513, 577

[56] References Cited

U.S. PATENT DOCUMENTS

| | | | |
|---|---|---|---|
| 2,148,294 | 2/1939 | McAllister et al. | 562/527 |
| 3,153,083 | 10/1964 | Smidt et al. | 562/577 |
| 3,492,325 | 1/1970 | Thompson et al. | 562/527 |

FOREIGN PATENT DOCUMENTS 50-28936 9/1975 Japan ............................ 562/527

*Primary Examiner*—Vivian Garner
*Attorney, Agent, or Firm*—Cushman, Darby & Cushman

[57] ABSTRACT

A novel process for producing pyruvic acid is provided in which process hydroxyacetone is oxidized with a molecular oxygen-containing gas in a water-containing or aqueous solvent in the presence of a catalyst. The catalysts useful for the above oxidation reaction are those composed of either at least one metal selected from the group consisting of platinum, palladium, rhodium, ruthenium, and rhenium, or the at least one metal admixed with at least one element selected from the group consisting of silver, tellurium, tin, bismuth, lead and indium or with a compound of the at least one element. The resulting pyruvate can be effectively isolated in the form of a solid by concentrating the reaction solution and adding the concentrate to isopropyl alcohol.

16 Claims, No Drawings

PROCESS FOR PRODUCING PYRUVIC ACID

BACKGROUND OF THE INVENTION

1. Field of the Invention

This invention relates to a novel process for producing pyruvic acid by oxidizing hydroxyacetone with a molecular oxygen-containing gas.

2. Description of the Prior Art

Heretofore, a number of processes of producing pyruvic acid have been proposed including, for example, (1) a process in which sodium cyanide and acetyl chloride are reacted to give acetyl cyanide and the cyanide is hydrolyzed, (2) a process for dry distilling tartaric acid in the presence of potassium hydrogensulfate, (3) a process using zymotechnics in which lactic acid is used as a starting material, (4) a process for oxidizing lactic acid such as with potassium permanganate, (5) a process for oxidizing ethylene glycol, and the like processes. However, the aforementioned processes have various drawbacks. More particularly the process (1) is disadvantageous in that the starting materials are expensive and by-products are produced in large amounts, resulting in low yield and making the separation and purification of the desired product difficult; In the process (2), the starting tartaric acid is expensive and large amount of potassium hydrogensulfate used as a subsidary material is consumed; In the process (3), α-ketoglutaric acid is secondarily produced; The process (4) is coped with difficulties that the potassium permanganate is consumed in larger amount than its chemical equivalent and that the product is contaminated with a manganese compound; and the process (5) for oxidizing ethylene glycol is not suitable for selective production of pyruvic acid since by-products other than pyruvic acid are formed in large amounts.

SUMMARY OF THE INVENTION

It is accordingly an object of the present invention to provide a novel process for producing pyruvic acid which overcomes the drawbacks of the prior art.

It is another object of the present invention to provide a process for producing pyruvic acid in which hydroxyacetone is oxidized in a solvent containing water.

It is a further object of the present invention to provide a catalyst suitable for oxidizing hydroxyacetone in a water-containing solvent.

It is a still further object of the present invention to provide a process for producing pyruvic acid using, as the starting hydroxyacetone source, an acetone-base waste from the phenol production process according to the cumene process.

It is another object of the present invention to provide a method for isolating a pyruvate in the form of a solid from the solution obtained after completion of the oxidation reaction.

According to the invention, there is provided a process for producing pyruvic acid which comprises oxidizing hydroxy-acetone with a molecular oxygen-containing gas in a solvent containing water in the presence of a catalyst to directly provide an aqueous solution of pyruvic acid or a pyruvate, the catalyst used being at least one platinum group element selected from platinum, palladium, rhodium, ruthenium, and rhenium, or a mixture of the at least one platinum group element and at least one element selected from the group consisting of silver, tellurium, tin, bismuth, lead, and indium or at least one compound thereof.

The hydroxyacetone used as the starting material may be the acetone-base waste produced from the phenol production process according to the cumene process. The reaction solution obtained after completion of the oxidation reaction is concentrated and then mixed with isopropyl alcohol to separate the resulting pyruvate as a solid or crystals.

According to one of the prominent features of the invention, an aqueous solution containing a pyruvate can be produced from hydroxyacetone conveniently from an industrial viewpoint and the pyruvate can be isolated as a solid.

Another prominent feature of the present invention is that, as described above, the acetone-base waste produced from the phenol production process according to the cumene process can be utilized as the starting hydroxyacetone source.

Pyruvic acid obtained according to the process of the invention is important as an intermediate in the course of substance metabolism in a living body or as a starting material for producing L-tryptophane by a fermentation method in which indole, pyruvic acid and ammonia are used as starting materials and are interacted by the action of tryptophanase. Further, pyruvic acid is also important and useful as a starting material for producing L-cysteine by zymotechnics together with ammonia and hydrogen sulfide or as a starting material for producing L-tyrosine also by zymotechnics together with phenol and ammonia.

DESCRIPTION OF THE PREFERRED EMBODIMENT

The catalyst useful in the process of the invention comprises at least one platinum group element selected from the group consisting of platinum, palladium, rhodium, ruthenium and rhenium or a mixture of the above-mentioned at least one platinum group element and, as a second and/or a third component, at least one element or compound of such element selected from the group consisting of silver, tellurium, tin, bismuth, lead, and indium. For example, the catalyst can be platinum, palladium or a mixture thereof. Also, a mixture of palladium, platinum or mixtures thereof and lead or a lead compound supported on activated carbon can be used as the catalyst for the oxidation.

These catalytic components or compositions may be employed without a carrier but it is industrially preferred to support them on carriers as usually employed. Examples of such carriers include activated carbon, alumina, diatomaceous earth, pumice, magnesia and the like. In most cases, activated carbon or alumina is preferably employed. The amount of the catalytic component on carrier is in the range of 0.1–20 wt %, preferably 1–10 wt %, where the at least one platinum group element is used. If at least one element selected from silver, tellurium, tin, lead and indium or compounds thereof are used, as a second and/or a third component, together with the above-indicated at least one platinum group element, the amount of the platinum group element is in the range of 0.5–20 wt %, preferably 1–10 wt %, and the total amount of the second and third components is in the range of 0.1–30 wt %, preferably 0.5–20 wt %.

The platinum group element is generally employed in the form of an element but may be used as compounds such as oxides. The second and/or third component may be in the form of elements or their compounds. Examples of the compounds are oxides, hydroxides, nitrates, sulfates, halides, carbonates, salts of organic acids and the like.

The catalysts useful in the process of the invention can be produced by a usual manner, for example, by impregnating alumina or active carbon with an aqueous solution of chloroplatinic acid, and, after drying, treating for reduction the impregnated carrier with formaline, hydrazine, or hydrogen gas. The catalyst containing the second and/or third component can be similarly produced by mixing, for example, an aqueous chloroplatinic acid solution and an aqueous silver nitrate solution in desired ratio, impregnating a carrier with the mixture, and then subjecting the carrier to a reduction treatment.

Commercially available noble metal catalysts may be likewise used in the practice of the invention. Needless to say, such commercially available noble metal catalyst which has been applied with the second and/or third component may be similarly used. The application is feasible by impregnating a commercially available powdery palladium-on-activated carbon catalyst with an aqueous solution of lead acetate or nitrate, or by adding a second and/or a third water-soluble compound to the reaction solution prior to commencement of the oxidation reaction.

The hydroxyacetone used as the starting material in the process of the invention may be obtained, for example, by dehydrogenating 1,2-propanediol in gas phase in the presence of a copper-base catalyst but can generally be obtained inexpensively as a by-product, contained in the acetone-base waste, from the phenol production process by the cumene process. Thus, according to the process of the invention, pyruvic acid can be produced conveniently from the by-product formed on production of phenol according to the cumene process.

Since, in the process of the invention, hydroxyacetone is oxidized in solvent in liquid phase, water is suitably used as the solvent. The hydroxyacetone contained in the waste from the cumene process is, of course, obtained in the form of an aqueous solution, so that the waste may be used as it is or after being concentrated to a desired level.

Aside from water, there may be used a mixed solvent of water and a solvent miscible with water such as dimethylformamide, diethyleneglycol dimethyl ether, dioxane or tertiary-butyl alcohol. In general, however, water alone is frequently used as the solvent since the use of water alone is advantageous industrially.

For the oxidation reaction, the concentration of hydroxyacetone in the aqueous solvent is in the range of 1-30 wt %, e.g., 2-15 wt % or 3-15 wt %, preferably 5-20 wt %. Less concentration of hydroxyacetone is unfavorable since a great deal of expense is needed to concentrate the reaction solution and an energy consumption such as for agitation of the reaction solution and feed of air increases. Larger hydroxyacetone concentration than that defined above is also unfavorable since the reaction rate is lowered with an increase of side reactions. Thus, the concentration within the above-defined range is used.

In practice, hydroxyacetone is oxidized with a molecular oxygen-containing gas in an aqueous or water-containing solvent in the presence of the afore-indicated catalyst. The amount of the catalyst is not critical but is in most cases in the range of 10–200 g, as a catalyst on carrier, per 1 l of the reaction solution. The catalyst may be filtered after the reaction and repeatedly employed over a long time.

In order to carry out the process of the invention, hydroxy acetone is oxidized, as described hereinbefore, with the molecular oxygen-containing gas in the aqueous solvent in the presence of the above-mentioned catalyst, whereupon the reaction is feasible in a wide pH range, i.e. under acidic, neutral or basic conditions. In this connection, however, the rate of the reaction becomes lower under neutral or acidic pH range. Accordingly, the reaction is generally conducted under neutral to basic conditions. For this purpose, an alkaline substance is added to the reaction solution. Examples of the alkaline substance include alkali metal hydroxides such as caustic alkalis, alkaline earth metal hydroxides such as barium hydroxide, alkali metal carbonates such as sodium carbonate, sodium bicarbonate, etc., and ammonium hydroxide. When the basicity of the reaction solution is too strong, the carbonyl radicals of the starting material and the final product may undergo side reactions such as condensation and thus the reaction solution is not desirable to be under too basic conditions. It is general to maintain the pH of the reaction solution neutral to weakly basic by adding an alkaline substance intermittently or continuously in an amount just required for neutralizing pyruvic acid produced as the reaction proceeds. Preferably, the pH is maintained in the range of 6–11, and most preferably 7–9.5, e.g., 8–9.5.

The oxidizing agent useful in the present invention is a molecular oxygen-containing gas such as oxygen gas, air, or oxygen gas or air diluted with an inert gas such as nitrogen.

The reaction temperature is in the range of room temperature to 100° C., e.g., 30°–100° C. or 30°–70° C., preferably 40°–70° C. Lower temperatures than the above-defined range are not practical since the reaction rate becomes too low. Higher temperatures are not favorable since by-products are produced in large amounts, resulting in lowering of the yield.

The reaction pressure is in the range of an atmospheric pressure to 10 kg/cm$^2$, preferably an atmospheric pressure to 5 kg/cm$^2$ (0.2–2 kg/cm$^2$ as a partial pressure of oxygen). Higher pressure (or higher partial pressure of oxygen) will increase the reaction rate but will accelerate lowering of the catalytic activity when the catalyst is repeatedly employed over a long time for reaction under high partial pressure of oxygen. Thus, the use of such higher pressure is not favorable.

The time required for the reaction varies depending mainly on the amount of catalyst and the reaction temperature but is generally in the range of 1–10 hours in the case of a batch system. Good result can be frequently obtained when the reaction is complete within 1–3 hours.

The process of the invention is feasible either by a batch system or a continuous system. In most cases the reactor used is of an agitated type or a bubbling tower type, while the catalyst bed is generally of a suspensoid type though a fixed bed type catalyst is usable.

The aqueous reaction solution after completion of the reaction is filtered to remove the catalyst therefrom and concentrated to obtain an aqueous solution of a pyruvate. This aqueous solution can be used, as it is, as a starting material for producing amino acids by zymotechnics. In order to produce free pyruvic acid, the aqueous pyruvate solution is neutralized with an acid or treated with an ion-exchange resin as by a usual manner.

The isolation of a pyruvate, e.g. sodium pyruvate, from the solution from which the catalyst has been removed by filtration is feasible as follows. In general, the pyruvates are poor in thermal stability, and it is difficult to separate the solid pyruvate from the reaction solution obtained by oxidation of hydroxyacetone only by evaporating the pyruvate-containing aqueous solution to dryness since it suffers from decomposition or decarboxylation, resulting frequently in side production of acetate or polymers. We have made an extensive study of the method of isolating the solid pyruvate from an aqueous solution containing the pyruvate and found that the solid pyruvate can be efficiently precipitated by mixing the aqueous solution with isopropyl alcohol.

The pyruvate can be isolated from the aqueous solution by the steps of mixing the aqueous pyruvate solution with isopropyl alcohol to allow the pyruvate to separate as solid or crystals, separating the solid from the solution, and washing it.

The medium for precipitating the pyruvate by mixing with the aqueous pyruvate solution should be isopropyl alcohol. Even if lower alcohols other than isopropyl alcohol, such as methanol, ethanol or butanol are used, it is impossible to precipitate the pyruvate as solid from the aqueous pyruvate solution or, even though partial precipitation takes place, the yield of the precipitate is extremely low, thus the use of such lower alcohols being impractical.

The aqueous pyruvate solution produced by the catalytic oxidation of hydroxyacetone in an aqueous solution generally contains an acetate as a by-product and small amount of unreacted hydroxyacetone. Though it is generally considered difficult to separate the pyruvate from the acetate so as to economically collect the pyruvate alone, the separation of the pyruvate from the acetate can be simultaneously realized according to the isolation technique using isopropyl alcohol since the acetate is relatively soluble in isopropyl alcohol.

If the aqueous reaction solution is colored considerably, it is preferred to subject the aqueous solution to a suitable decolorization treatment such as, for example, a treatment with activated carbon prior to the isolation in isopropyl alcohol. When isopropyl alcohol is mixed with the aqueous solution without the decolorization treatment, the precipitate is colored.

The concentration of the aqueous pyruvate with which isopropyl alcohol is to be mixed is generally in the range of 20-70 wt %, preferably 30-50 wt %. Isopropyl alcohol suitable for the above purpose is not necessary to be highly pure alcohol but is sufficient to be a water-containing one. Accordingly, the mixed waste solution of isopropyl alcohol once employed and water can be simply distilled to recover an azeotropic mixed solution composed of 88% of isopropyl alcohol and 12% of water for repeated use. The recovery of isopropyl alcohol for reuse needs no special extraction and distillation procedures as described above.

The amount of isopropyl alcohol is in the range of 2-10 parts by volume, preferably 4-6 parts by volume, per part by volume of the aqueous pyruvate solution or aqueous pyruvate slurry.

In practice, isopropyl alcohol is agitated, to which the aqueous pyruvate solution is added while continuing the agitation, thereby precipitating white crystals of the pyruvate. The precipitate is aged while agitating the solution for a while and then separated by filtration. The precipitate obtained by the filtration is washed with anhydrous isopropyl alcohol or acetone and air-dried at room temperature to 60° C. or dried under reduced pressure.

The present invention will be particularly illustrated by way of the following examples.

EXAMPLE 1

The acetone-base waste from the phenol production process according to the cumene process was concentrated to obtain an aqueous solution containing 10 wt % of hydroxyacetone. 200 g of the aqueous solution and 7.5 g of a 5 wt % platinum-on-activated carbon powder catalyst were charged into a 1 l stainless steel cylinder for reaction. The stainless steel cylinder was equipped with a baffle plate, an agitator having turbine blades, an air-feeding device, and pH electrodes and was heated from outside in a water bath to maintain the content at a predetermined temperature. The reaction was conducted at a temperature of the solution of 45° C. at an injected air rate of 400 cc/min under a normal pressure while agitating at 750 r.p.m. Separately, 10.8 g of sodium hydroxide was dissolved in 20 cc of distilled water to provide an aqueous solution.

The aqueous sodium hydroxide solution was charged intermittently such that the pH was invariably held at 8-9 during the course of the reaction.

90 minutes after commencement of the reaction, about 80% of the aqueous sodium hydroxide solution was charged. Up to that time, the reaction proceeded in the zero-order reaction with regard to the concentration of hydroxyacetone. When 80% of the aqueous sodium hydroxide solution was consumed, the rate of reaction became suddenly low. Accordingly, the charge of the alkali was stopped, followed by continuing the reaction for further 10 minutes. As a result, the pH of the reaction solution was lowered to 7.5. The catalyst was filtered off from the reaction solution and then the concentration of pyruvic acid in the reaction solution was quantitatively determined by a high speed liquid chromatography, revealing that 14.0 g of sodium pyruvate and 2 g of sodium acetate were produced. The reaction solution was concentrated to 40 cc under reduced pressure and then introduced into 150 cc of isopropyl alcohol while agitating. The resulting sodium pyruvate precipitate was separated by filtration, washed with isopropyl alcohol, and dried at 50° C. to obtain 12.8 g of white powder. The infrared spectrum of the white powder coincided with that of a authentic sample. When the nuclear magnetic resonance spectroscopy was conducted by dissolving the white powder in heavy water, an absorption alone based on the proton in the methyl group of pyruvic acid was observed with slight degree of an absorption based on the proton in the methyl group of acetic acid.

EXAMPLE 2

20 g of commercially available hydroxyacetone and 7.0 g of a 5 wt % palladium and lead carbonate-on-carrier catalyst were charged into the same type of reactor as used in Example 1 for reaction at 45° C. in the same manner as in Example 1. The injected air rate and agitation speed were similar to those of Example 1.

The catalyst employed was prepared as follows.

7.0 g of commercially available 5 wt % palladium-on-activated carbon powder catalyst was suspended in 200 g of distilled water, into which an aqueous solution obtained by dissolving 400 mg of lead nitrate in 10 g of distilled water was dropped under sufficient agitation. Then, an aqueous solution dissolving 1 g of sodium carbonate therein was added to the suspension and agitated for 30 minutes. The catalyst was separated by filtration, sufficiently washed with water, and employed for the reaction.

The oxidation reaction was continued for 95 minutes while maintaining the pH of the reaction solution at 8.5-9.3, during which 83% of an aqueous solution dissolving 10.8 g of sodium hydroxide was consumed. Up to that time, the reaction proceeded in the zero-order reaction with regard to hydroxyacetone. The charge of the alkali was stopped and the reaction was continued for further 15 minutes, so that the pH of the reaction solution was lowered to 7.8. The reaction was stopped and the catalyst was removed by filtration. The reaction solution was analyzed by a high speed liquid chromatography, revealing that 14.5 g of sodium pyruvate and 2.0 g of sodium acetate were formed. Similarly to the case of Example 1, isopropyl alcohol was used for crystallization to obtain 13.0 g of the precipitate. The thus obtained white precipitate was subjected to an infrared spectrum analysis, with the result that the infrared absorption spectrum of this product coincided with that of an authentic substance. Further, the NMR spectroscopy revealed that the amount of the acetate in the precipitate was very small.

The above process was repeated 23 times using the same catalyst repeatedly. In the 23rd cycle of the reaction process, it was found that the catalyst was held in its catalytic activity to a level of 75% of the initial activity and it was thus possible to use such catalyst for further reaction.

EXAMPLE 3

The acetone-base aqueous waste from the phenol production process according to the cumene process was concentrated to give an aqueous solution containing 10 wt % of hydroxyacetone.

A stainless steel container having an inner volume of 3 l and equipped with a baffle plate, an air feeding device and a turbine blade agitator was used as a reactor. 80 g of 1 wt % ruthenium on powder active carbon and 2 l of an aqueous hydroxyacetone solution were charged into the reactor and reacted at a reaction temperature of 40° C. while injecting air under a normal pressure with agitation.

In order to maintain the pH of the reaction solution to 7-8, an aqueous solution dissolving 100 g of sodium hydroxide in 200 ml of water was added portion by portion.

The time required for addition of 80% of the aqueous caustic soda solution was 2 hours. This means that 80% of the charged hydroxyacetone was converted into a corresponding carboxylic acid in 2 hours. At this time, the reaction was stopped and the catalyst was separated by filtration from the reaction solution. The reaction solution was analyzed by a high speed liquid chromatography and quantitatively determined, with the following result that 70%, 20% and the remaining 10% of the reacted hydroxyacetone were converted into sodium pyruvate, sodium acetate, and a condensed product, respectively.

EXAMPLES 4 AND 5

The same reactor and reaction procedure as in Example 1 were used but the following catalysts were used instead. The test results are shown in Table 1 below.

TABLE I

| Example No. | Catalyst* | Conversion of hydroxyacetone (mole %) | Selectivity to sodium pyruvate (mole %) |
|---|---|---|---|
| 4 | Rh/C | 75 | 71 |
| 5 | Re/C | 68 | 65 |

Note:
*Catalyst composed of 2 wt % of a platinum group element supported on activated carbon powder.

EXAMPLE 6

A stainless steel cylindrical container having an inner volume of 500 ml and equipped with a baffle plate, an air feeding device and a turbine blade agitator was used as a reactor.

150 ml of an aqueous 5% solution of hydroxyacetone secondarily produced from the phenol production process according to the cumene process and 3.0 g of commercially available 5 wt % palladium-on-carbon powder catalyst were charged into the reactor. Air was charged at a rate of 400 ml/min and the rate of oxidation of hydroxyacetone into pyruvic acid was determined at a reaction temperature of 45° C. while agitating at 750 r.p.m. During the reaction, an aqueous sodium hydroxide solution was charged into the reaction system portion by portion to maintain the pH of the reaction solution to 9.0-9.3. The relation between the reaction time and the conversion is shown in Table 2.

EXAMPLE 7

The reaction was conducted using the same device and reaction conditions as in Example 6 and the catalyst prepared as follows. That is, 3.0 g of the same type of the 5 wt % palladium-on-carbon powder catalyst as used in Example 6 was suspended in 100 ml of distilled water. To the suspension was added an aqueous solution of 180 mg of lead nitrate dissolved in 20 ml of distilled water under agitation, to which was further added a solution of 0.8 g of sodium hydroxide in 20 ml of distilled water. The mixture was agitated for 30 minutes. The aqueous solution was filtered and the solid matter was washed with distilled water to obtain a palladium-lead-carbon powder catalytic composition. The results obtained by the use of the catalyst, i.e. the relation between the reaction time and the conversion, are shown in Table 2.

TABLE 2

| | Conversion of Hydroxyacetone to Pyruvic Acid (mole %) | | | | |
|---|---|---|---|---|---|
| | Reaction time (min.) | | | | |
| Example No. | 15 | 30 | 45 | 60 | 90 |
| 6 | 25 | 35 | 44 | 50 | 59 |
| 7 | 37 | 56 | 68 | 79 | 91 |

EXAMPLES 8 AND 9

The reaction was conducted using the same device and reaction conditions as in Example 6 except that a 5% palladium-on-carbon powder catalyst or a 2% platinum-on-carbon powder catalyst was used in order to determine the time required for attaining 50% conversion of hydroxyacetone. The results are shown in Table 3.

EXAMPLE 10

The reaction was conducted using the same device and reaction conditions as in Example 6 except in that a Pd-Ag-Al$_2$O$_3$ catalytic composition which had been obtained by applying 3.0 g of a 5% palladium-on-alumina catalyst with 120 mg of silver nitrate by immersion techniques was used. The time required for attaining 50% conversion of hydroxyacetone was determined with the results shown in Table 3.

EXAMPLES 11-14

Example 1 was repeated using the catalysts indicated in Table 3. The time required for attaining the 50% conversion of hydroxyacetone was determined with the results shown in Table 3 below.

TABLE 3

| Example No. | Catalyst | Time required for attaining 50% conversion (min.) | Remarks |
|---|---|---|---|
| 8 | Pd-alumina | 43 | |
| 9 | Pd-Ag-alumina | 25 | |
| 10 | Pt-carbon | 47 | |
| 11 | Pt-Te-carbon | 24 | 200 mg of telluric acid was applied to 3.0 g of catalyst by impregnation. |
| 12 | Pd-Sn-carbon | 25 | 200 mg of tin oxychloride was applied to 3.0 g of catalyst by impregnation. |
| 13 | Pd-Bi-carbon | 28 | 150 mg of bismuth oxychloride was applied to 3.0 g of catalyst by impregnation. |
| 14 | Pd-In-carbon | 26 | 100 mg of indium chloride was applied to 3.0 g of catalyst by impregnation. |

EXAMPLE 15

200 g of an aqueous 10% hydroxyacetone solution and 5 g of 5 wt % palladium activated carbon powder catalyst were charged into a bubbling tower type reactor and air was blown thereinto under a normal pressure for reaction at a temperature of 50° C. An aqueous solution dissolving 10 g of sodium hydroxide in 20 cc of water was charged into the reactor portion by portion to neutralize pyruvic acid produced by the reaction for conversion into sodium pyruvate. The pH of the reaction solution was invariably maintained in the range of 8-9.

After completion of the reaction, the catalyst was removed by filtration and the resulting solution was analyzed by a high speed liquid chromatography, revealing that the conversion of hydroxyacetone was 70%, the selectivity to sodium pyruvate was 70%, and the selectivity to sodium acetate was 15%.

The reaction solution was passed through a column packed with activated carbon for decolorization and concentrated to 40 g. The concentrate was added to 150 g of isopropyl alcohol to precipitate white crystals. The crystals were allowed to stand for 5 hours, separated by filtration, and dried at 40° C. under reduced pressure to obtain 8 g of white powder of sodium pyruvate. The thus obtained powder was dissolved in heavy water and subjected to an NMR spectroscopy. As a result, it was found that the content of sodium acetate was small and sodium pyruvate was highly pure.

What is claimed is:

1. A process for producing pyruvic acid comprising oxidizing at room temperature to 100° C. hydroxyacetone with a molecular oxygen-containing gas in a solvent containing water in the presence of a catalyst composed of either (a) at least one element selected from the group consisting of platinum, palladium, rhodium, ruthenium and rhenium or (b) a mixture of (a) with at least one element selected from the group consisting of silver, tellurium, tin, bismuth, lead and indium or a compound thereof.

2. A process according to claim 1 wherein the temperature is 30° to 70° C.

3. A process according to claim 2 wherein the temperature is 40° to 70° C.

4. A process for producing pyruvic acid comprising oxidizing hydroxyacetone with a molecular oxygen-containing gas in a solvent containing water in the presence of a catalyst composed of a mixture of at least one element selected from the group consisting of platinum, palladium, rhodium, ruthenium and rhenium and at least one element selected from the group consisting of silver, tellurium, tin, bismuth, lead and indium or a compound thereof.

5. A process according to claim 4, wherein said catalyst is composed of a mixture of palladium, platinum or a mixture thereof and, lead or a lead compound, said mixture being supported on activated carbon.

6. A process according to claim 1 or 4, wherein there is employed platinum, palladium or a mixture thereof.

7. A process according to claim 1 or 4 wherein the catalyst is composed of palladium supported on activated carbon or alumina or a mixture of palladium supported on activated carbon or alumina and at least one element selected from the group consisting of silver, tellurium, tin bismuth, lead and indium or a compound thereof.

8. A process according to claim 1 or 4, wherein said molecular oxygen-containing gas is air.

9. A process according to claim 1 or 4, wherein the pH of the reaction solution is in the range of 7-9.5.

10. A process according to claim 1 or 4, wherein an alkali metal hydroxide is added to the reaction system intermittently or continuously during the course of the reaction to maintain the pH of the reaction solution in the range of 7-9.5.

11. A process according to claim 1 or 4, wherein the reaction temperature is in the range of 30°-100° C.

12. A process according to claim 1 or 4, wherein the reaction pressure is in the range of atmospheric pressure to 5 kg/cm$^2$ and the oxygen partial pressure is in the range of 0.2-2 kg/cm$^2$.

13. A process according to claim 1 or 4, wherein the starting hydroxyacetone source is an acetone-base aqueous waste from the production of phenol from cumene.

14. A process according to claim 1 or 4, wherein the concentration of hydroxyacetone in the solvent containing water is in the range of 2 to 15 wt %.

15. A process for producing pyruvic acid comprising contacting an aqueous solution containing 3 to 15 wt % of hydroxyacetone with a molecular oxygen-containing gas at a temperature of 30° to 70° C. under a pressure of atmospheric pressure to 5 kg/cm$^2$ in the presence of a catalyst composed of palladium and a lead compound supported on activated carbon while adding intermittently or continuously a caustic alkali during the course of the reaction to maintain the pH of the reaction solution in the range of 8-9.5.

16. A process according to claim 1, 4 or 15, further comprising, after removing the catalyst by filtration, adjusting the concentration of the pyruvate in the reaction solution to a range of 20 to 70%, and adding the thus concentrated solution or slurry to isopropyl alcohol in an amount of 2–10 times that of the solution to separate said pyruvate as crystals.

* * * * *